United States Patent [19]

Lange et al.

[11] 4,071,762

[45] Jan. 31, 1978

[54] SCINTILLATION CAMERA WITH IMPROVED OUTPUT MEANS

[75] Inventors: Kai Lange, Vedbaek, Denmark; Ernest J. Wiesen, Wauwatosa; Eric M. Woronowicz, West Allis, both of Wis.

[73] Assignee: General Electric Company, Schenectady, N.Y.

[21] Appl. No.: 731,150

[22] Filed: Oct. 12, 1976

[51] Int. Cl.² .................. G01T 1/20; G01T 1/164
[52] U.S. Cl. .................. 250/369; 250/363 S
[58] Field of Search .................. 250/363 S, 369

[56] References Cited

U.S. PATENT DOCUMENTS

| | | | |
|---|---|---|---|
| 3,732,419 | 5/1973 | Kulberg et al. | 250/369 X |
| 3,851,177 | 11/1974 | Van Dijk et al. | 250/369 X |
| 3,911,278 | 10/1975 | Stout | 250/369 X |
| 3,984,689 | 10/1976 | Arseneau | 250/369 |

Primary Examiner—Archie R. Borchelt
Attorney, Agent, or Firm—Ralph G. Hohenfeldt

[57] ABSTRACT

In a scintillation camera system, the output pulse signals from an array of photomultiplier tubes are coupled to the inputs of individual preamplifiers. The preamplifier output signals are coupled to circuitry for computing the $x$ and $y$ coordinates of the scintillations. A cathode ray oscilloscope is used to form an image corresponding with the pattern in which radiation is emitted by a body. Means for improving the uniformity and resolution of the scintillations are provided. The means comprise biasing means coupled to the outputs of selected preamplifiers so that output signals below a predetermined amplitude are not suppressed and signals falling within increasing ranges of amplitudes are increasingly suppressed. In effect, the biasing means make the preamplifiers non-linear for selected signal levels.

8 Claims, 5 Drawing Figures

SCINTILLATION CAMERA WITH IMPROVED OUTPUT MEANS

BACKGROUND OF THE INVENTION

This invention relates to scintillation cameras which are commonly called gamma cameras. The invention is particularly concerned with improving the uniformity and resolution of scintillation cameras.

In nuclear medicine, scintillation cameras are used to detect gamma ray photons emitted from a body in which a radioisotope has been infused. The photons are emitted in correspondence with the extent to which the isotope is absorbed by the tissue under examination. With proper processing, signals corresponding with the photons may be used to develop a point-by-point image, corresponding with the emission pattern, on a cathode ray oscilloscope. A common camera system in use today is based on the camera of Anger as disclosed in U.S. Pat. No. 3,011,057. The Anger camera comprises an array of photosensitive devices such as photomultiplier tubes, usually hexagonally arranged, having their input ends adjacent a light conducting plate or disc. Beneath the disc is a scintillation crystal which converts incoming gamma photons into light photons or scintillations. A collimator is interposed between the scintillator and the body so that photons emitted by the body will impinge perpendicularly on the planar scintillation crystal.

The scintillations are detected by the array of individual photomultiplier tubes which view overlapping areas of the crystal, and well-known electronic circuits are used to convert the outputs of the photomultiplier tubes into x and y coordinate signals which are used to control a cathode ray oscilloscope in such manner that each point source of light formed on the oscilloscope tubes correspond with a point at a similar location in the crystal or on the body. The output signals are also used to develop a z signal which turns on the oscilloscope tube in accordance with the computed coordinates. The z signal is developed only if the energy of the scintillation event falls within a predetermined energy window. A photographic film may be used as an integrator of the large number of light spots appearing on the screen of the oscilloscope. A substantial number of scintillation events is required to make up the final picture of radioactivity distribution in the body tissue.

One problem in existing scintillation camera systems is that when a source of radioactivity having uniform distribution is placed close to the crystal disc and a photograph is made of the oscilloscope, the photograph will show non-uniformity which is characterized by "hot spots" under each photomultiplier tube and cold spots between the tubes. In other words, a spot or scintillation event actually occurring between the photomultiplier tubes is sensed as being partially shifted under the tubes, causing a decrease in spot density between the tubes and an apparent increase in spot density under the tubes. This phenomenon can be mitigated by moving the photomultiplier tubes further from the disc, but this decreases the ability of the camera to resolve small details. Hence, if small details are to be resolved and if uniformity or correspondence between the generated and displayed image patterns is to be maintained, the normal electric signals that exist in the system must be modified or corrected.

One method of obtaining correction with non-electronic means is illustrated in U.S. Pat. No. 3,774,032 which is assigned to the assignee of the present invention. In this patent the distribution of light as perceived by the photomultiplier tubes is altered by placing masks between the crystal and photomultiplier tubes so that light from certain areas of the scintillator crystal cannot go directly to the photomultiplier tubes. This reduces the output of the tubes for scintillations occurring directly under them but it permits light from other areas, that is, from between the tubes to go directly to the tubes. The result is better resolution and uniformity in the image.

It has been proposed heretofore to achieve the results obtained in the cited patent by use of electronic correction means. Without electronic or other correction, scintillations occurring in areas between the tubes appear to be, by inherent geometric phenomena, nearer to the tubes. This is manifested by what is called nonuniformity of the displayed image. More particularly, the image derived from a uniformly distributed isotope source is more dense or concentrated immediately under and near the tubes than in between the tubes. Electronic correction is further based on recognition that if the input and output signals of the preamplifiers are linearly related, the disproportionality between brightness and distance remains, but if the output is modified so that low level signals corresponding with noise are eliminated and high level signals corresponding with the scintillation event occurring at or near the center of the tube are suppressed, more uniform distribution of the light spots on the display will be accomplished. It has been proposed and demonstrated in the prior art that if the output of the preamplifiers is properly biased, high level signals can be clipped or suppressed which, in effect, amounts to reducing the gain of the preamplifiers for high amplitude signals or signals above a predetermined amplitude. Thus, the plot of preamplifier input signal versus preamplifier output signal is linear for a first comparatively low level signal range and it has a break point in it after which gain is reduced for higher level input signals.

A system using the single break point concept has been made and tested and found to produce better results than were obtainable with linear amplification over the entire input signal range. However, uniformity and resolution were still not optimized for there was still some evidence of nonuniformity or concentration of light spots where they should have been uniformly distributed. In other words, there were still localized "hot" and "cold" spots which appeared randomly throughout the crystal, varying from system to system and depending upon the individual characteristics of the components of the system.

SUMMARY OF THE INVENTION

A preferred embodiment of the present invention is based on the recognition that more than one change in slope of the input to output transfer characteristic of the preamplifiers can eliminate the small localized hot and cold spots which still existed when known techniques for eliminating them were employed. Thus, in accordance with the invention, two or more selected bias voltages are applied to the output of selected preamplifiers to optimize uniformity and resolution.

It is a general object of this invention to improve the uniformity or accuracy of correspondence between the light dots that comprise a displayed image with the positions of the scintillations which correspond with radiation absorption events.

Another object is to improve the resolution of a scintillation camera.

How these and other more specific objects of the invention are achieved will appear in the course of the ensuing description of a preferred embodiment of the invention which will now be set forth in reference to the drawings.

DESCRIPTION OF A PREFERRED EMBODIMENT

Figure 3:
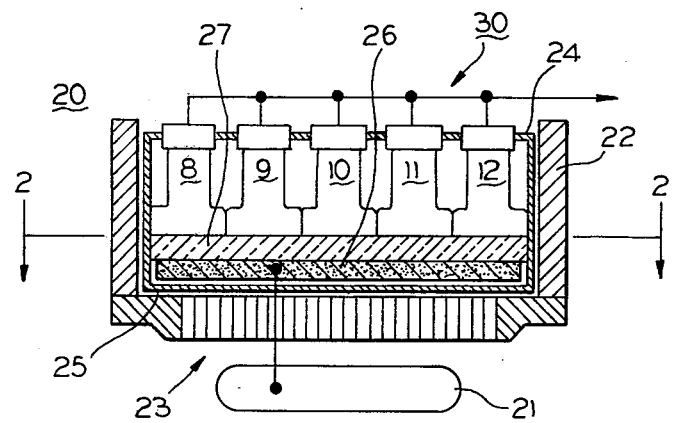
FIG. 3 is a schematic side view of a detector head of a scintillation camera.
Figure 2:
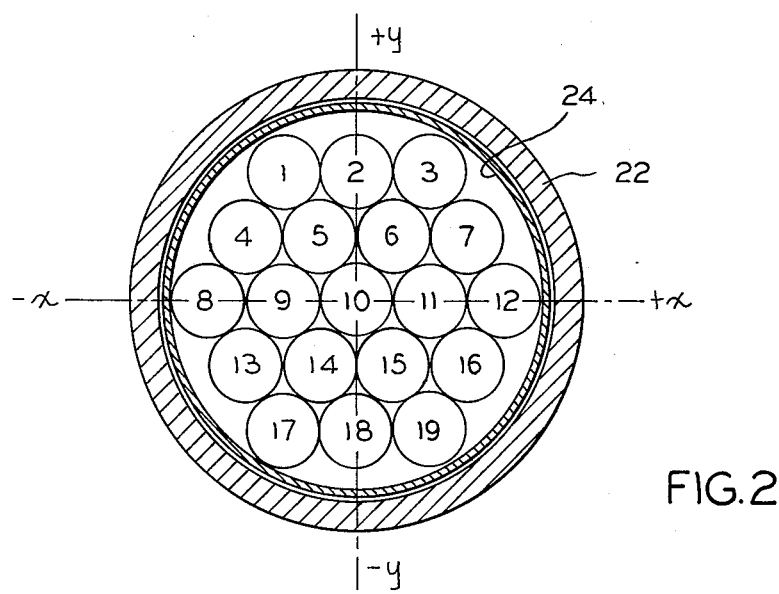
FIG. 2 is a schematic diagram of a hexagonally arranged array of photomultiplier tubes in a scintillation camera.

FIGS. 2 and 3 show a schematic transverse section and an elevation view of a scintillation camera with which the new circuitry may be used. In FIG. 3 the scintillation camera is generally designated by the reference numeral 20. It is disposed over a body 21. The body or an organ thereof is assumed to have absorbed a radioactive isotope and that the distribution of the isotope and, hence, the configuration of the tissue that absorbed it is to be imaged. The isotope emits gamma ray photons which are intercepted by the gamma camera 20. The camera comprises a radiation opaque housing 22. Fastened to the bottom of the housing is a collimator 23 comprised of an array of gamma radiation permeable tubes with impermeable material between them. Inside of the housing is a closed container 24 which has a gamma ray photon permeable bottom 25. Immediately above bottom 25 is a planar disc 26 made of crystalline material such as thallium activated sodium iodide which produces a scintillation at any point where it absorbs a gamma ray photon. An array of photosensitive devices such as photomultiplier tubes 1–19 are situated above scintillator crystal 26. The photomultiplier tubes are coupled to crystal 26 with a light pipe 27 which may consist of a glass plate. Scintillations in crystal 26 are detected by the tubes which each produce pulse output signals for each scintillation event.

As can be seen in FIG. 2, an array consisting of 19 photomultiplier tubes are used in this example and they are arranged hexagonally about a central tube 10. As is well-known, a common number of tubes used in a scintillation camera is 19 but cameras with 37 photomultiplier tubes are also used. The present invention has application in systems using 19 or 37 or other numbers of tubes.

Figure 1:
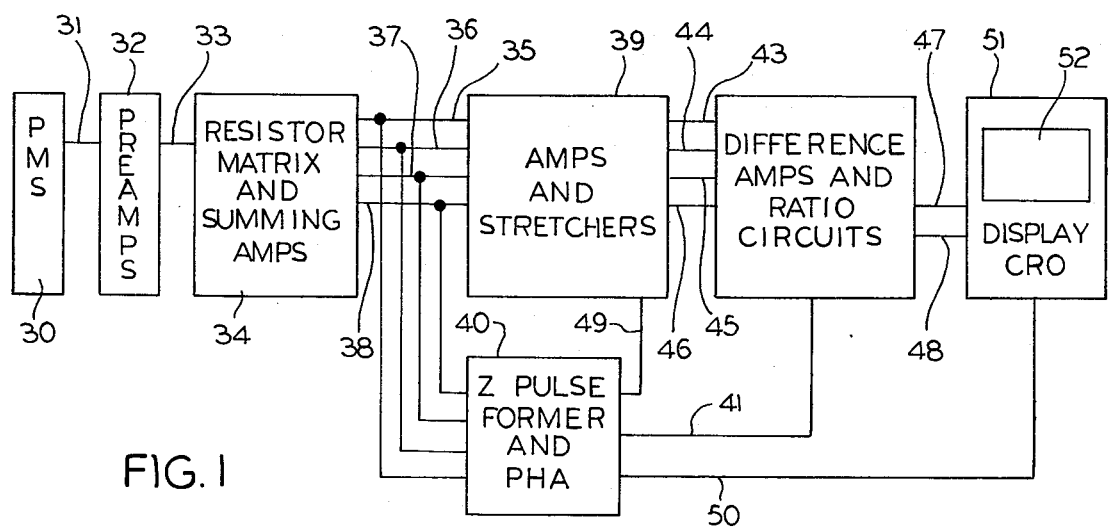
FIG. 1 is a block schematic diagram of a scintillation camera system in which the invention may be employed.

FIG. 1 is a block diagram of the main components of a scintillation camera system in which the invention may be used. As indicated, the 19 photomultiplier tubes which, in this FIGURE, are indicated collectively by the number 30, cooperate to detect each scintillation and their 19 outputs 31 are separately coupled to individual preamplifier circuits 32. The 19 preamplifier outputs 33 are coupled to a resistor matrix and summing amplifier circuit 34 which develops from the preamplifier outputs, four coordinate output signals $+x$, $-x$, $+y$, and $-y$ on lines 35–38. These four output signals are fed to line amplifiers and gated stretchers 39 and to a z pulse former and pulse height analyzer (PHA) 40. The z pulse former combines the four input signals into a z signal which corresponds with the energy of a scintillation event. The z signal is supplied by means of line 41 to difference amplifier and ratio circuits 42. The pulse height analyzer 40 gates the gated stretchers if the energy of a scintillation event falls within a selected energy window so that stretched $+x$, $-x$, $+y$, and $-y$ signals on lines 43–46 may be fed to the difference amplifiers and ratio circuits 42 where the $+x$ and $-x$ signals and $+y$ and $-y$ signals are subtracted and the results ratioed with the z pulses as the denominator to produce x and y coordinate signals on line 47 and 48. The pulse height analyzer 40 also produces an unblanking signal on line 50 which is fed to a display cathode ray oscilloscope (CRO) 51 when the analyzer has determined that a scintillation event falls within a selected energy window and the display CRO then produces a spot of light on its screen 52 at the x and y coordinates which have been computed.

The system just outlined is basically well-known to those involved in design and use of scintillation camera systems.

Figure 4:
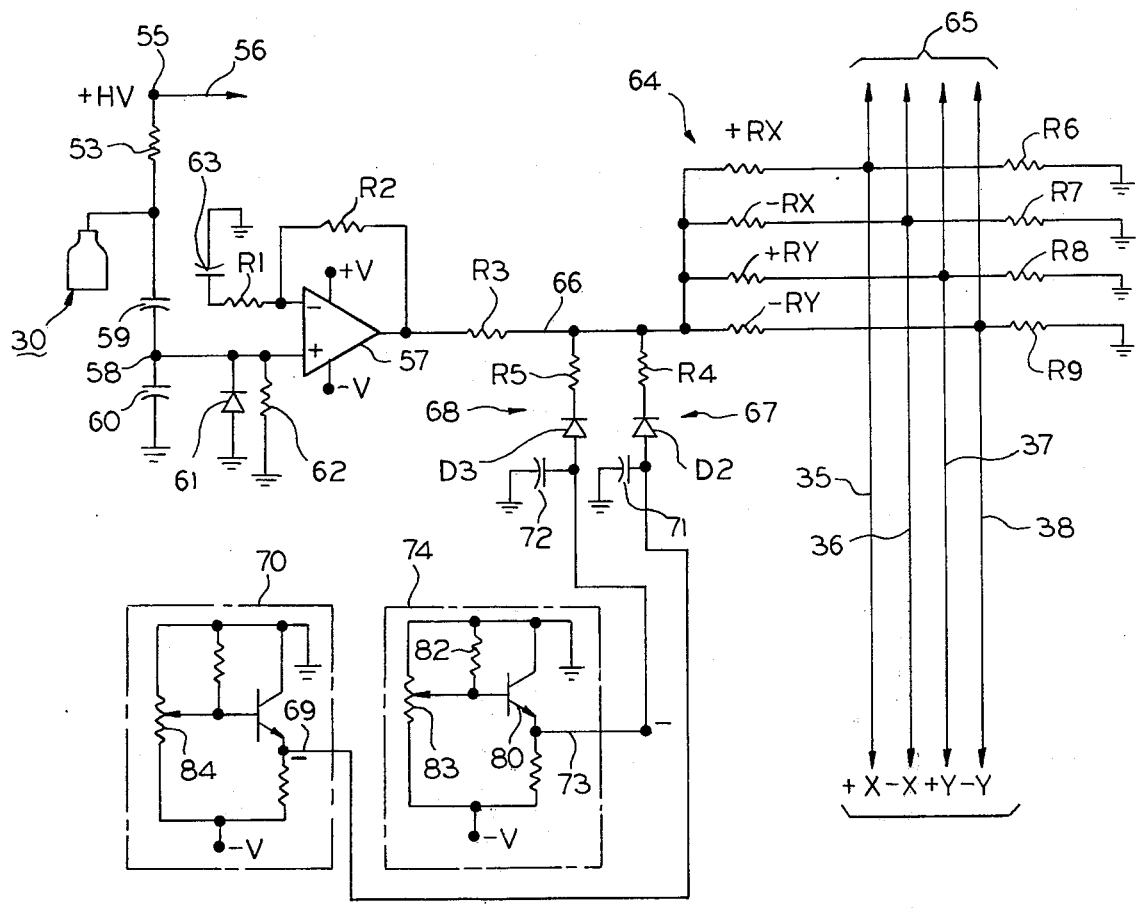
FIG. 4 is a circuit diagram in which the new features are employed.

One channel for developing signals corresponding with the x and y coordinates of the scintillations detected by one photomultiplier tube is depicted in FIG. 4. Some parts of this circuitry are well-known in the art. Typically a channel comprises an input photomultiplier tube 30 of a well-known multiple dynode type. The anode of photomultiplier tube 30 is connected through a resistor 53 to a high voltage source terminal 55 which, as indicated by the arrowhead line 56 also connects to all of the other photomultiplier tubes in the 19 tube array 30. The output pulse signals from photomultiplier tubes 30 are supplied to the noninverting input of a signal converting means which comprises an operational amplifier 57 that serves as a preamplifier. The signals are coupled to preamplifier 57 from the intermediate point 58 of a capacitive voltage divider comprised of capacitors 59 and 60. The input of amplifier 57 is protected against excess voltage with a diode 61. A bias resistor 62 for establishing zero offset is also provided. The preamplifier has a feedback circuit comprised of resistors R2 and an input resistor R1 and is ac coupled to ground with a capacitor 63.

As is known, the amplitudes of the pulse signals from photmultipliers 30 depends on the distance of a particular scintillation event in the scintillation crystal 26 from the photomultiplier tube under consideration. In the absence of the new features of the circuitry, input signals to the amplifier 57 are amplified linearly which, as was explained earlier, results in giving weight to the signal in correspondence with the apparent distance of the scintillation event from the photomultiplier tube, but this does not correspond with the real distance and leads to error. As was also explained, there is a bunching effect in direct alignment with the photomultiplier tubes which is manifested by hot spots in a CRO display even though the isotope source is uniform. Hot spots still exist although the highest amplitude signals are suppressed with the use of prior art single step suppression techniques.

Whether or not the new features of the circuitry which will be explained are used, the output signals from the preamplifiers 57 are conducted through a resistor R3 to a resistor matrix 64 which is involved in computing the x and y coordinates of the scintillation event that produced the pulse signal. A typical resistor matrix is illustrated. It comprises four voltage dividers. The dividers are comprised of resistors +RX, R6, −RX, R7; +RY, R8; and −RY, R9. As is well-known by those using matrixes of this kind in scintillation camera systems, the resistors in the RX and RY pairs are weighted so that they are representative of or correspond with the reciprocal of the distance of the particular photomultiplier tube from the Y or X axes of the photomultiplier tube array 30. As shown in FIG. 2, the Y axis passes through the center point of tubes 2, 10 and 18 and the X axis passes through the center points of tubes 8–12. The midpoints of the dividers are connected to common lines 35–38. Each of the photomultiplier tube channels has an associated resistor matrix 64 with its particularized value resistors connected to common lines 35–38. For instance, the ends 65 of the common lines will connect to resistor matrixes associated with each of the other photomultiplier tubes in the array 30. The output signals on lines 35–38, which are indicative of the x and y coordinates of the scintillations, are supplied to the amplifier and pulse stretchers which are symbolized by the block 39 in FIG. 1. Then, in accordance with known practice, coordinates of a scintillation are used to create a light spot at a corresponding position on the screen 52 of the CRO.

The new means for obtaining non-linear amplification or output from preamplifiers 57 for photomultiplier tube pulse output signals falling within two or more amplitude ranges will now be discussed. The lowest level signals are amplified linearly by preamplifiers 57 and pass without modification to the resistor matrixes 64. A diode, not shown, could be inserted between the outputs of preamplifiers 57 and R3 so that noise signals below the diode forward voltage threshold are blocked. In accordance with the invention, the output lines 66, connecting the outputs of preamplifiers 57 to the resistor matrixes have bias voltages selectively applied to them. In this example, two biasing means 67 and 68 are shown. Biasing means 67 comprises diode D2 and resistor R4 which are connected in series between the lines 66 and the output terminal 69 of a bias or threshold voltage source 70. A filter capacitor 71 is connected between the bias voltage source 70 and ground. The voltage at the output terminal 69 of bias voltage source 70 is set at a threshold value which is slightly negative with respect to ground in this example. Diode D2 is, thus, normally reverse biased. Incoming pulse signals from the photomultiplier tubes 30 drive the output of preamplifiers 57 negatively. Output pulse signals which are less than the negative bias or threshold voltage applied through diode D2 are applied by way of line 66 at their full amplitude to resistor matrix 64. However, signals at the output of preamplifiers 57 which are sufficiently negative to exceed the bias source threshold voltage cause diode D2 to become forward biased to thereby limit the amplitude of the signal or, to effectively reduce the gain of the preamplifiers for signals that are more negative than the negative voltage applied through D2.

The other biasing means 68 comprised of R5, diode D3 and a filter capacitor 72 is connected to the output terminal 73 of a second bias voltage source which establishes a second threshold voltage. Source 74 is set so that the bias voltage appearing on its output 73 is slightly more negative than the bias voltage on output terminal 69 of the other voltage source 70. Diode D3 is reversed biased to a greater extent than diode D2. Hence, diode D3 becomes forward biased when the output signals from the preamplifiers 57 are somewhat more negative than is required to forward bias diode D2.

The bias voltage sources 70 and 74 are similarly constructed but, as has been explained, their outputs are set at different threshold voltage levels. Batteries or other stable voltage sources could be used in place of sources 70 and 74. In this example, source 74 comprises a transistor 80 having its collector connected to ground or the midpoint of a dual voltage power supply, not shown. The bias voltage is developed across an emitter resistor 81. Fixed base-emitter bias is supplied through resistor 82 and this bias is made adjustable for controlling output voltage by use of a potentiometer 83. The output bias voltage of the other source 70 is set with a potentiometer 84.

Those skilled in the art will appreciate that in cases where the pulse output signals from the preamplifiers 57 are positive going, diodes D2 and D3 would be poled oppositely and bias sources 70 and 74 would be arranged to supply positive bias voltages on their output terminals 69 and 73, respectively instead of negative voltages as in this example.

Figure 5:
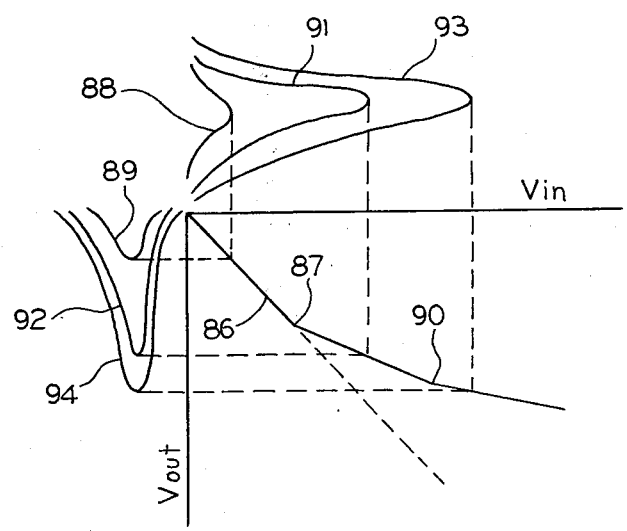
FIG. 5 is a graph showing the relationships of the output signals from the preamplifiers for the photomultiplier signals versus the input signals in accordance with the invention.

FIG. 5 shows graphically how the gain of the preamplifiers is affected by use of the two biasing means 67 and 68. It will be seen that a first low range of input signals from the photomultiplier tubes will be amplified linearly as evidenced by the first segment 86 of the transfer characteristic curve having a constant slope up to a first break point 87 where the bias voltage applied to diode D2 is less negative or more positive than the output signals. Hence, input signals such as 88 in a first range up to break point 87 are amplified linearly as shown by the corresponding output signal 89. The break point at which the bias of diode D3 is overcome is marked 90 on the graph. Thus, any input voltage such as 91 having a peak in a second range between break points 87 and 90 will undergo decreased or non-linear amplification as can be seen from tracing the dashed lines extending from the input signal 91 to the corresponding output signal 92. When diode D3 becomes forward biased, corresponding with break point 90, the slope of the transfer characteristic or the effective gain of the preamplifier again changes to a lesser value. Thus, any input signal such as 93 having a peak in a third range greater than the break point 90 will undergo less amplification as evidenced by the corresponding output signal 94. Additional steps of bias voltage could be used such that there would be more than two break points in the transfer characteristic, but good results have been obtained with only two break points. If a diode, not shown, were placed in series with the output of preamplifier 57 to eliminate response to low level noise, line 86 would start at a small offset from the zero axis in FIG. 5.

Specific values of the bias voltages applied to diodes D2 and D3 would depend on the characteristics of a particular circuit. However, in a practical embodiment, the desired results have been obtained by setting the lower bias voltage on output terminals 69 at about one-half of the peak voltage of the outputs from the preamplifiers 57. The second bias voltage on terminal 73 was set at about 0.7 of peak signal voltage. Peak signal voltage may be determined by opening the D2 and D3 series circuits and making a measurement of the maximum signal that is obtainable at the outputs of preamplifiers 57 or by biasing diodes D2 and D3 to a larger value than peak voltage. Then the diodes circuits are closed and the potentials of the biasing sources are adjusted with potentiometers 83 and 84 until a uniform display on the display tube 52 with a uniform radioisotope source is obtained.

The relatively higher of the two bias voltages, that is, the voltage from source 74 is applied only to the preamplifier outputs 57 for the central cluster of photomultiplier tubes in FIG. 2, in other words, to the preamplifiers for tubes 10, 5, 6, 11, 15, 14 and 9 in a nineteen tube array. The lower bias voltage supplied by source 70 is applied to the preamplifier outputs of all of the remaining tubes. However, for tubes 1, 3, 8, 12, 17 and 19 the value of R4 is about 30% lower than the value of R4 in the circuit to preamplifiers 57 associated with photomultiplier tubes 2, 4, 7, 13 and 18. Thus, voltage division resulting from action by the divider R4 and R3 is slightly different from one group of tubes than for another. In a practical embodiment, 1 kilohm resistors were used for R4 and R5 and most of the tubes and a value of 1.3 kilohms was used for R4 in preamplifier circuits associated with photomultiplier tubes 2, 4, 7, 13 and 18.

The field of view of the scintillation camera shown in FIG. 2 falls substantially within a circle that is slightly inside of the centers of tubes 4, 13, 18, 16, 7 and 2. Other tubes at the edge of the array do not contribute very much signal. Scintillations are only detected if they occur on the inside of the outer tubes. This accounts for the manner in which the bias voltages are applied as discussed in the last paragraph. In any event, it will be evident that the photomultiplier tubes which make the greatest contribution to signal are suppressed most, which means that hot spots are reduced and resolution is improved. In scintillation cameras using 37 or some number of photomultiplier tubes in excess of 19, the central clusters of tubes within the hexagonal array would have their preamplifier 57 outputs subjected to the higher bias or threshold voltage and rings of peripheral tubes would be biased less. Although the foregoing selective connection arrangement is preferred, good results are also obtained if all of the tubes are treated in the same manner.

Although a particular scheme for producing multiple break points in the transfer characteristics of the photomultiplier tube preamplifiers has been described in considerable detail, such description is inteded to be illustrative rather than limiting for the attainment of multiple break points may be variously achieved. Hence, the scope of the invention is to be determined only by construing the claims which follow.

We claim:

1. Radiation imaging apparatus including means for producing scintillations in response to intercepted radiation, a plurality of photosensitive devices arranged adjacent each other on one side of said means for producing scintillations, said devices producing electric pulses, respectively, in response to occurrence of each scintillation, the positional relationship of said devices relative to said means for producing scintillations being such as to cause distortion in the relationship between the coordinates of the scintillations and the electric pulses,
    signal converting means having input means for receiving said electric pulses as input signals and having output means, said signal converting means producing output signals which are generally representative of the coordinates of said scintillations,
    first means responsive to occurrence of input signals above a first range of amplitudes and within a higher second range of amplitudes by altering the gain of said signal converting means such that signals in said second range are suppressed to thereby improve correspondance between said signals and the coordinates of said scintillations, and
    second means responsive to occurrence of input signals in a third range of amplitudes higher than said second range by further altering the gain of said converting means such that the signals in said third range are suppressed to thereby further improve correspondance between said signals and the coordinates of said scintillations.

2. The apparatus as in claim 1 wherein:
    said first means includes a biasing device having output means coupled with said output means of said signal converting means and having input means,
    a first source of bias voltage coupled to said input means of said first means,
    said second means including another biasing device having output means coupled with said output means of said signal converting means and having input means, and
    a second source of bias voltage having a different magnitude than said first source of bias voltage, said second source being coupled with said input means of said biasing device in said second means.

3. The apparatus as in claim 2 wherein:
    said first bias voltage has a value such that the gain of said signal converting means is altered when the output signals therefrom are at or above about 50% of the peak signal amplitudes expected from said converting means, and said second bias voltage has a value such that the gain is further altered when the output signals from said converting means are at or above about 70% of the peak signal amplitude expected therefrom.

4. Radiation imaging apparatus including means for producing scintillations in response to intercepted radiation, a plurality of photsensitive devices arranged adjacent each other on one side of said means for producing scintillations, said tubes producing electric pulses, respectively, in response to occurrence of each scintillation, the positional relationship of said devices relative to said means for producing scintillations being such as to cause distortion in the relationship between the coordinates of scintillations and the electric pulses,
    preamplifier means having input means for receiving said electric pulses as input signals and having output means, said preamplifier means producing output signals which are generally representative of the coordinates of said scintillations,
    a first bias voltage source,
    a first biasing means coupling said first source to said output means of said preamplifier means, said first biasing means becoming conductive whenever the magnitude of the output signal of said preamplifier means exceeds the magnitude of said first bias voltage to thereby reduce the gain of said amplifier means for a second range of signal amplitudes which is above a first range of amplitudes,
    a second bias voltage source for providing a voltage that is higher than the voltage of said first source,
    a second biasing means coupling said second source to said output of said preamplifier means, said second biasing means becoming conductive whenever the magnitude of the output signal exceeds the magnitude of the second bias voltage, to thereby reduce further the gain of said amplifier means for a third range of signal amplitudes which are in a higher amplitude range than said second range.

5. The apparatus as in claim 4 wherein each of said biasing means includes a diode.

6. The apparatus as in claim 4 wherein said first biasing voltage has a value of about 50% of the value of a predetermined peak signal from the output of said preamplifier means and said second biasing voltage has a value of about 70% of said peak signal.

7. The apparatus as in claim 4 wherein said photosensitive devices are in a generally hexagonal arrangement wherein one substantially hexagonally arranged inner group is surrounded by another substantially hexagonally arranged outer group, said higher voltage source being coupled through said biasing means only of preamplifier means output means for photosensitive devices in said inner group and said lower voltage source being coupled through biasing devices only to preamplifier output means for photosensitive devices outside of said inner group.

8. The apparatus as in claim 7 wherein there are 7 photosensitive devices in said inner group and 12 in said outer group.

* * * * *